US00PP25204P3

(12) United States Plant Patent
Hernandez

(10) Patent No.: US PP25,204 P3
(45) Date of Patent: Dec. 30, 2014

(54) *AGAPANTHUS* PLANT NAMED 'HINESAG1'

(50) Latin Name: *Agapanthus africanus*
Varietal Denomination: HinesAg1

(75) Inventor: David Hernandez, Orange, CA (US)

(73) Assignee: Hines Growers, Inc., Fallbrook, CA (US)

( * ) Notice: Subject to any disclaimer, the term of this patent is extended or adjusted under 35 U.S.C. 154(b) by 143 days.

(21) Appl. No.: 13/385,985

(22) Filed: Mar. 19, 2012

(65) Prior Publication Data

US 2013/0247265 P1 Sep. 19, 2013

(51) Int. Cl.
*A01H 5/00* (2006.01)

(52) U.S. Cl.
USPC ..... Plt./398

(58) Field of Classification Search
USPC ..... Plt./398
See application file for complete search history.

*Primary Examiner* — June Hwu
*Assistant Examiner* — Louanne Krawczewicz Myer
(74) *Attorney, Agent, or Firm* — Barbara Campbell; Cochran Freund & Young LLC

(57) ABSTRACT

An *Agapanthus* plant particularly distinguished by large, bluish-purple inflorescences, and yellow and green variegated foliage, is disclosed.

1 Drawing Sheet

Genus and species: *Agapanthus africanus.*
Variety denomination: 'HinesAg1'.

BACKGROUND OF THE NEW PLANT

The present invention comprises a new and distinct variety of *Agapanthus*, botanically known as *Agapanthus africanus*, and hereinafter referred to by the variety name 'HinesAg1'. The new variety originated as a sport from tissue culture of *Agapanthus africanus* 'Hinag', commercially known as SUMMER GOLD 'Hinag' (U.S. Plant Pat. No. 10,866) in June 1999 in Irvine, Calif.

The new plant was first asexually propagated in Irvine, Calif. in 1999 and has been asexually reproduced by divisions for approximately 12.5 years in Irvine, Calif. The present invention has been found to retain its distinctive characteristics through successive asexual propagations by divisions.

'HinesAg1' has not been made publicly available or sold more than one year prior to the filing of this application.

SUMMARY

The following are the most outstanding and distinguishing characteristics of the new variety when grown under normal horticultural practices in Irvine, Calif.

1. Large, bluish-purple inflorescences; and
2. Yellow and green variegated foliage.

DESCRIPTION OF THE PHOTOGRAPHS

This new *Agapanthus* plant is illustrated by the accompanying photographs which show the overall plant habit, foliage and inflorescence of the plant. The colors are as true as can be reasonably obtained by conventional photographic procedures. The photographs are of a 3-year old plants grown outdoors in Irvine, Calif. in May 2010.

DESCRIPTION OF THE NEW VARIETY

Figure 1:
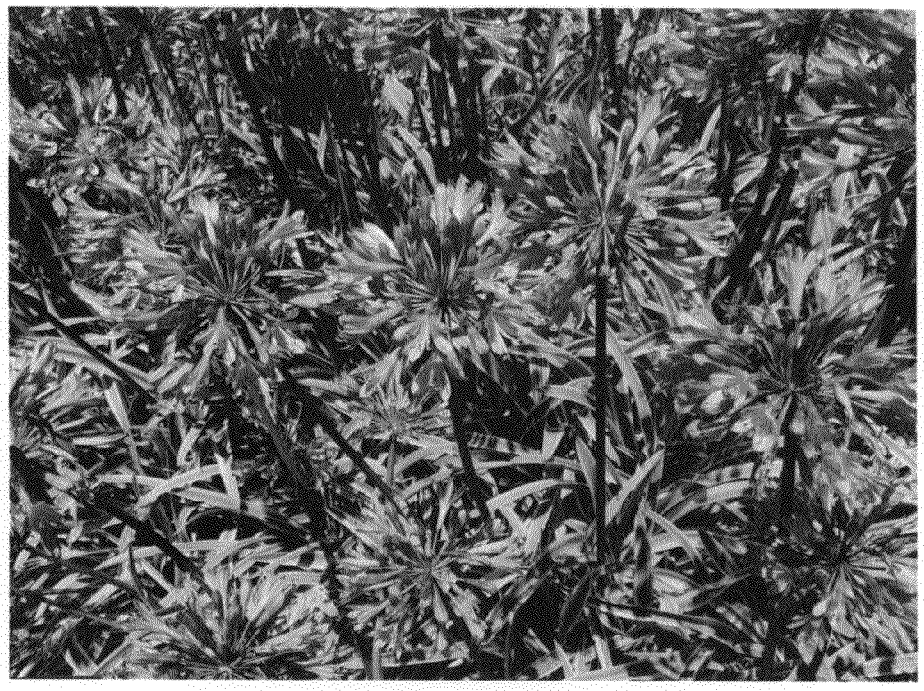
FIG. 1 shows a the whole plant, including the habit, foliage and inflorescence.
Figure 2:
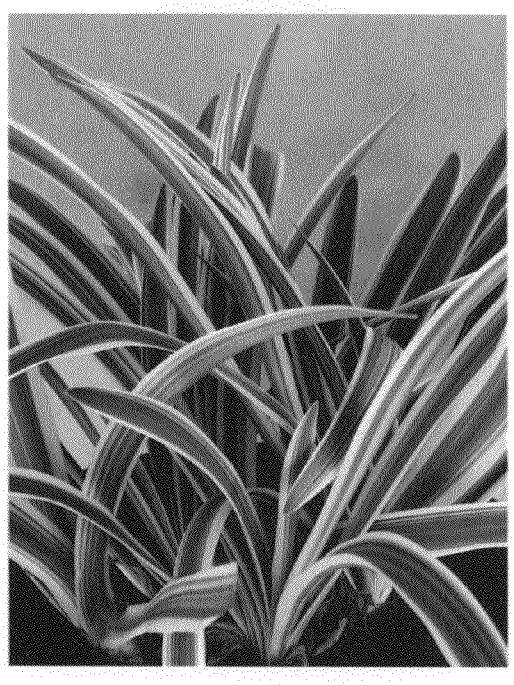
FIG. 2 shows a close-up of the foliage.

The following detailed descriptions set forth the distinctive characteristics of 'HinesAg1'. The data which defines these characteristics were collected from asexual reproductions carried out in Irvine, Calif. The plant history was taken in January 2012 on 1-year old plants grown outdoors in Irvine, Calif. Color references were taken under natural light and are to The R.H.S. Colour Chart of The Royal Horticultural Society of London (R.H.S.), fifth edition (2007). Texture descriptions were taken using a dissecting microscope.

Classification:
- *Family.*—Amaryllidaceae.
- *Botanical name.*—*Agapanthus africanus.*
- *Common name.*—African lily.
- *Denomination.*—'HinesAg1'.

Parentage:
- *Parent.*—*Agapanthus africanus* 'Hinag', commercially known as SUMMER GOLD 'Hinag' (U.S. Plant Pat. No. 10,866).

Plant:
- *Propagation type.*—Divisions.
- *Plant height.*—About 41.7 cm to top of the foliage; if including the inflorescence, about 64.5 cm to 72.5 cm.
- *Plant spread/diameter.*—3 feet to 4 feet.
- *Growth rate.*—Medium vigorous.
- *Temperature tolerances.*—Zones 8 to 10.

Foliage:
- *Quantity of blades per plant.*—11.
- *Arrangement.*—Basal.
- *Length.*—45.7 cm.
- *Width.*—3.2 cm to 3.8 cm.
- *Shape of blade.*—Linear.
- *Margin.*—Entire.
- *Apex.*—Acute.
- *Base.*—Sheathed.
- *Texture (both upper and lower surfaces).*—Smooth.

*Venation pattern* (*both upper and lower surfaces*).—Linear.

*Color* (*both upper and lower surfaces*).—Random stripes of RHS 146A, RHS 148C, RHS 148B and RHS 13C.

Inflorescence:

*Inflorescence type*.—Round umbel composed of many individual flowers.

*Habit*.—Upright.

*Number of flowers per inflorescence or umbel*.—81 to 92.

*Number of scapes per plant*.—1.

*Typical and observed flowering season*.—Spring to summer.

*Fragrance*.—Absent.

*Height*.—6.5 cm.

*Width*.—14.0 cm.

*Flower depth*.—6.0 cm to 8.0 cm (including the 2.8 cm stem).

*Flower width*.—3.3 cm.

*Bud*.—Color: RHS 92B and RHS 94B. Length: From less than 1.0 cm to 2.5 cm. Shape: Elongated having a rounded end (the end is the part not attached to the pedicel).

*Tepals*.—Arrangement and quantity per flower: Seven arranged in a single whorl with the tepals fused into a narrow tube. Length: 2.5 cm; unfused length is 2.2 cm. Width: Unfused width is 0.6 cm to 0.8 cm. Base: Fused. Apex: Rounded. Shape: Spatulate. Margin: Entire. Color (when opening and fully mature): Upper surface: RHS 97D and RHS 93C. Lower surface: RHS 91B and RHS 93C.

*Flower tube length*.—2.8 cm to 3.9 cm.

*Pedicels*.—Length: 2.6 cm to 3.0 cm. Diameter: 3.1 mm to 4.7 mm. Color: RHS 137C and RHS 148D. Strength: Strong. Texture: Smooth.

*Peduncle*.—Length: 58.0 cm to 66.0 cm. Diameter: 2.8 mm to 5.0 mm. Color: RHS 148C, RHS 144A, and RHS 145D. Strength: Strong. Texture: Smooth.

Reproductive organs, seeds, and disease/pest resistance:

*Stamens*.—Quantity per flower: 7. Anther length: 4.0 cm. Filament color: RHS 92D. Pollen amount and color: Moderate.

*Pistil quantity*.—1 per flower. Stigma quantity: 1 per flower. Style length: 2.1 cm. Style color: RHS 84D, RHS 93D, and RHS 92A. Ovary color: RHS 145C.

*Seed*.—Shape: Mainly long oval-shaped. Color: RHS 202A. Length: 6.0 cm. Width: 1.5 cm to 2.0 cm.

*Disease and pest resistance or susceptibility*.—None observed.

COMPARISON WITH PARENTAL AND COMMERCIAL VARIETY

'HinesAg1' differs from the parent 'Hinag' (U.S. Plant Pat. No. 10,866) in that 'HinesAg1' has a taller plant height (31.0 cm) than 'Hinag' (about 18.0 cm).

'HinesAg1' differs from the commercial comparison 'Benfran' (U.S. Plant Pat. No. 21,705) in that 'HinesAg1' has a longer leaf blade (45.7 cm) than 'Benfran' (30.0 cm).

I claim:

1. A new and distinct variety of *Agapanthus* plant as shown and described herein.

* * * * *